United States Patent
Gao et al.

(10) Patent No.: US 10,671,918 B2
(45) Date of Patent: Jun. 2, 2020

(54) ATTENTION BASED SEQUENTIAL IMAGE PROCESSING

(71) Applicant: International Business Machines Corporation, Armonk, NY (US)

(72) Inventors: Peng Gao, Beijing (CN); Xiu Li Li, Beijing (CN); Yong Qin, Beijing (CN); Shi Lei Zhang, Beijing (CN); Xiaolu Zhang, Beijing (CN); Xin Zhang, Beijing (CN); Shi Wan Zhao, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 136 days.

(21) Appl. No.: 15/792,051

(22) Filed: Oct. 24, 2017

(65) Prior Publication Data

US 2019/0122103 A1 Apr. 25, 2019

(51) Int. Cl.
*G06K 9/00* (2006.01)
*G06N 3/08* (2006.01)
(Continued)

(52) U.S. Cl.
CPC .............. *G06N 3/08* (2013.01); *G06K 9/6228* (2013.01); *G06K 9/6256* (2013.01);
(Continued)

(58) Field of Classification Search
USPC ....................................................... 328/128
See application file for complete search history.

(56) References Cited

U.S. PATENT DOCUMENTS 8,570,393 B2 10/2013 Moed et al.
8,625,869 B2 1/2014 Harder et al.
(Continued)

FOREIGN PATENT DOCUMENTS

CN 101383008 A 3/2009
EP 3166049 A1 5/2017

OTHER PUBLICATIONS

Romera-Paredes et al., "Recurrent Instance Segmentation," Oct. 24, 2016, 24 pages. https://arxiv.org/pdf/1511.08250.pdf.

*Primary Examiner* — Stephen P Coleman
(74) *Attorney, Agent, or Firm* — Amin, Turocy & Watson, LLP

(57) ABSTRACT

Techniques facilitating attention based sequential image processing are provided. A system can comprise a memory that stores computer executable components and a processor that executes the computer executable components stored in the memory. The computer executable components can comprise an initialization component that can perform self-attention based training on a model that comprises context information associated with a sequence of images. Images of the sequence of images can be selected during the self-attention based training. The computer executable components can also comprise a localization component that can extract local information from the images selected during the self-attention based training based on the context information. In addition, the computer executable components can also comprise an integration component that can update the model based on an end-to-end integrated attention training framework comprising the context information and the local information.

16 Claims, 10 Drawing Sheets

(51) Int. Cl.
    *G06N 3/04*     (2006.01)
    *G06T 7/00*     (2017.01)
    *G06K 9/62*     (2006.01)
    *G16H 50/20*    (2018.01)
    *G16H 40/63*    (2018.01)
    *G16H 20/70*    (2018.01)
    *G06K 9/46*     (2006.01)

(52) U.S. Cl.
    CPC ............ *G06K 9/6296* (2013.01); *G06N 3/04* (2013.01); *G06T 7/0012* (2013.01); *G16H 20/70* (2018.01); *G16H 40/63* (2018.01); *G16H 50/20* (2018.01); *G06K 9/46* (2013.01); *G06T 2207/10016* (2013.01); *G06T 2207/20076* (2013.01); *G06T 2207/20081* (2013.01); *G06T 2207/20084* (2013.01)

(56) References Cited

U.S. PATENT DOCUMENTS

| | | | |
|---|---|---|---|
| 2009/0292198 A1* | 11/2009 | Kleiven | A61B 5/031 600/416 |
| 2010/0122277 A1* | 5/2010 | Fonseca | G11B 27/105 725/10 |
| 2016/0232440 A1 | 8/2016 | Gregor et al. | |
| 2016/0350336 A1 | 12/2016 | Checka et al. | |
| 2017/0011281 A1* | 1/2017 | Dijkman | G06K 9/66 |
| 2017/0046855 A1* | 2/2017 | Cao | G06T 7/60 |
| 2017/0169315 A1 | 6/2017 | Vaca Castano et al. | |
| 2017/0262996 A1* | 9/2017 | Jain | G06T 7/143 |
| 2017/0308770 A1* | 10/2017 | Jetley | G06K 9/4671 |
| 2018/0005393 A1* | 1/2018 | Senthamil | G06T 19/006 |
| 2018/0316502 A1* | 11/2018 | Nadeau | G06N 20/00 |

\* cited by examiner

ATTENTION BASED SEQUENTIAL IMAGE PROCESSING

BACKGROUND

The subject disclosure relates to image processing, and more specifically to attention based sequential image processing.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, apparatuses, and/or computer program products that facilitate attention based sequential image processing are provided.

According to an embodiment, a system can comprise a memory that stores computer executable components and a processor that executes the computer executable components stored in the memory. The computer executable components can comprise an initialization component that can perform self-attention based training on a model that comprises context information associated with a sequence of images. Images of the sequence of images can be selected during the self-attention based training. The computer executable components can also comprise a localization component that can extract local information from the images selected during the self-attention based training based on the context information. In addition, the computer executable components can also comprise an integration component that can update the model based on an end-to-end integrated attention training framework. The end-to end integrated attention framework can comprise the context information and the local information.

According to another embodiment, a computer-implemented method can comprise performing, by a system operatively coupled to a processor, self-attention based training on a model that comprises context information associated with a sequence of images. Images of the sequence of images can be selected during the self-attention based training. The computer-implemented method can also comprise extracting, by the system, local information from the images selected during the self-attention based training based on the context information. Further, the computer-implemented method can comprise updating, by the system, the model based on an end-to-end integrated attention training framework comprising the context information and the local information.

According to a further embodiment, a computer program product that facilitates attention based sequential image processing is provided. The computer program product can comprise a computer readable storage medium having program instructions embodied therewith, the program instructions can be executable by a processing component to cause the processing component to perform self-attention based training on a model that comprises context information associated with a sequence of images. Images of the sequence of images can be selected during the self-attention based training. The program instructions can also cause the processing component to extract local information from the images selected during the self-attention based training based on the context information. Further, the program instructions can cause the processing component to update the model based on an end-to-end integrated attention training framework comprising the context information and the local information.

DETAILED DESCRIPTION

Figure 1:
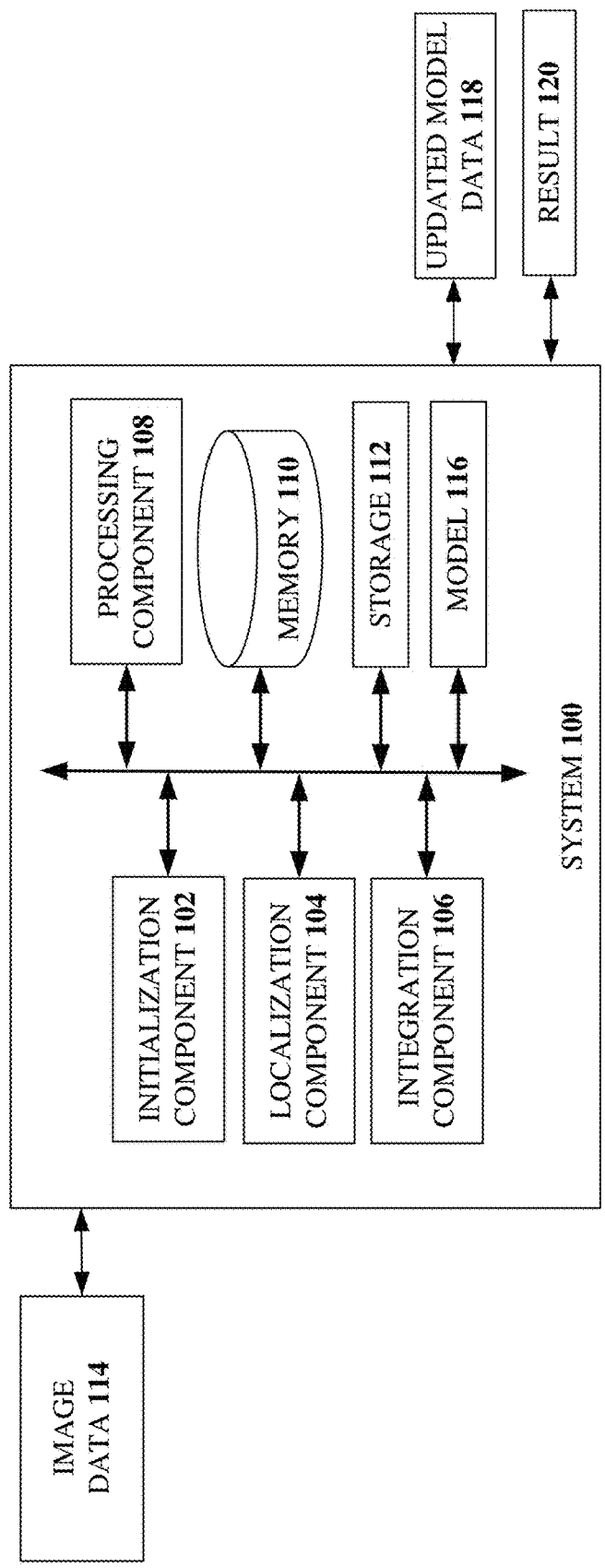
FIG. 1 illustrates a block diagram of an example, non-limiting system that facilitates training a model for attention based sequential image processing in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

As discussed herein images, such as digital images, can be received and a model can be trained on the images. An output of the model can relate to interpretation of salient features of the images. The images can be a sequence of related images. In an example, the sequence of images can be medical images and interpretation of the salient features can comprise a medical diagnosis and/or a suggested medical treatment. For example, the sequence of images can be cross-section images of a human lung that together can represent an entire view of the human lung. It is noted that although various embodiments of the subject disclosure are described in association with sequential medical image processing, it should be appreciated that the disclosed techniques can be applied to other types of implementations for which sequential image processing can be utilized.

According to an implementation, provided is attention based sequential image processing. Both context information and local information can be taken into consideration during the sequential image processing. The context information can be information about the received images (e.g., the sequence of images). The local information can be one or more portions of at least one image of the sequence of images.

As discussed herein Recurrent Neural Network (RNN) training can be performed using sequential images as input and self-attention based RNN prediction state sequences can be run on a model. Then, an attention Convolutional Neural Network (CNN) for local image with sequential information as input can be trained. Further, the model can be updated by an end-to-end integrated attention training framework. According to an implementation, the sequential attention can also use local information as input.

Embodiments described herein comprise systems, computer-implemented methods, and computer program products that can perform image processing on received images. Specifically, one or more of the aspects can perform attention based sequential image processing through training of a model that can analyze multiple images received as input and can drill down into one or more salient or important features of one or more images of the multiple images. For example, the various aspects can exploit an attention mechanism to handle sequential image data. An advantage of the disclosed aspects is that the length of images can be variant (e.g., do not need to be a fixed image length). Further, the attention network can be utilized to predict the result directly. In addition, attention weight can be utilized to predict the attention information of a specific image.

FIG. 1 illustrates a block diagram of an example, non-limiting system 100 that facilitates training a model for attention based sequential image processing in accordance with one or more embodiments described herein. Aspects of systems (e.g., the system 100 and the like), apparatuses, or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

In various embodiments, the system 100 can be any type of component, machine, device, facility, apparatus, and/or instrument that comprises a processor and/or can be capable of effective and/or operative communication with a wired and/or wireless network. Components, machines, apparatuses, devices, facilities, and/or instrumentalities that can comprise the system 100 can include tablet computing devices, handheld devices, server class computing machines and/or databases, laptop computers, notebook computers, desktop computers, cell phones, smart phones, consumer appliances and/or instrumentation, industrial and/or commercial devices, hand-held devices, digital assistants, multimedia Internet enabled phones, multimedia players, and the like.

In various embodiments, the system 100 can be a sequential image processing computing system associated with technologies such as, but not limited to, computing technologies, artificial intelligence technologies, object classification technologies, medicine technologies, materials technologies, manufacturing technologies, supply chain and logistics technologies, financial services technologies, and/or other digital technologies. The system 100 can employ hardware and/or software to solve problems that are highly technical in nature (e.g., sequentially process a multitude of related images to focus on specific portions of one or more of the multitude of related images to determine a final result, performing self-attention based training on a model, updating the model based on an end-to-end integrated attention training framework), that are not abstract and that cannot be performed as a set of mental acts by a human. For example, images received can be complex images that have not previously been analyzed by the system 100, and which comprise a multitude of elements, including hidden layer states, all of which could be potentially of interest, and which can be difficult (if not impossible) to distinguish with the human eye. Further, the number of images received can be a large volume, which a human could not possibly automatically (e.g., within a matter of seconds or less) and consistently accurately process as discussed herein (e.g., analyze the multitude of sequential images and output a result based on a model trained on the multitude of sequential images). Further, in certain embodiments, some of the processes performed can be performed by one or more specialized computers (e.g., one or more specialized processing units, a specialized computer with a classification computing component, a specialized recurrent neural network component, a specialized convolutional neural network component, and so on) to carry out defined tasks related to machine learning and image processing as discussed herein.

The system 100 and/or components of the system 100 can be employed to solve new problems that arise through advancements in technologies mentioned above, computer architecture, and/or the like. One or more embodiments of the system 100 can provide technical improvements to computing systems, learning classifier systems, circuit systems, processor systems, artificial intelligence systems, recurrent neural network systems, convolutional neural network systems, and/or other systems. One or more embodiments of the system 100 can also provide technical improvements to a processor by improving processing performance of the processor and/or improving processing efficiency of the processor. According to some implementations, one or more embodiments of the system 100 can provide technical improvements to a processor by improving sequential image processing accuracy and/or facilitating sequential image processing efficiencies.

In the embodiment shown in FIG. 1, the system 100 can comprise an initialization component 102, a localization component 104, an integration component 106, a processing component 108, a memory 110, and/or a storage 112. The memory 110 can store computer executable components and instructions. The processing component 108 (e.g., a processor) can facilitate execution of the instructions (e.g., computer executable components and corresponding instructions) by the initialization component 102, the localization component 104, the integration component 106, and/or other system components. As shown, in some embodiments, one or more of the initialization component 102, the localization component 104, the integration component 106, the processing component 108, the memory 110, and/or the storage 112 can be electrically, communicatively, and/or operatively coupled to one another to perform one or more functions of the system 100.

The initialization component 102 can receive, as input data, image data 114. For example, the image data 114 can comprise a sequence of images. The images included in the sequence can be related images. By way of example and not limitation, the images can be a computed tomography scan (CT) scan of a patient's lungs (or another portion of the body). The CT scan uses computer-processed combinations of a multitude of X-ray measurements taken from different angles to produce cross-sectional images of specific areas of a scanned object (e.g., in this example the lungs). Accordingly, the image data 114 received by the initialization component 102 can include a sequence of the cross-sectional images.

Based on the image data 114, the initialization component 102 can perform self-attention based training on a model 116. According to some implementations, the model 116 can comprise context information, which can be associated with the sequence of images (e.g., the image data 114). For example, context information can include a sequence of images associated with a defined subject (e.g., a medical patient) and related metadata. Further, context information can include hidden layer state data. According to some implementations, hidden layer state data can include metadata that can be embedded within the sequence of images. Metadata can describe one or more elements within images of the sequence of images and, therefore, cannot be discerned with the human eye and/or cannot be evaluated in the human mind.

As mentioned, the initialization component 102 can perform self-attention based training on the model 116. During the self-attention based training, images of the sequence of images (e.g., image data 114) can be selected. To select the images, the initialization component 102 can evaluate the context information for features that can be relevant to a result. For example, the sequence of images can comprise thirty images and during the self-attention based training, the initialization component 102 can select a subset of images (e.g., four images) that can be relevant for determination of a result (e.g., a diagnosis of a patient, a root cause of a problem).

The localization component 104 can extract local information from the images selected during the self-attention based training by the initialization component 102. The local information can comprise features of the images determined by the localization component 104 to be relevant for training the model 116. According to some implementations, the localization component 104 can apply respective attention weights to the sequence of images. According to some implementations, respective hidden layer state information for the sequence of images can be used as input to the localization component 104 to determine the respective attention weights.

The attention weights can indicate respective levels of importance of the images of the sequence of images. For example, a first image assigned a first attention weight can be more important for training the model than a second image assigned a second attention weight, where the first attention weight is more than the second attention weight. However, the disclosed aspects are not limited to this embodiment and other manners of ranking the attention weights can be utilized, such as, for example, a lower attention weight indicates a higher level of importance.

The integration component 106 can update the model 116 based on an end-to-end integrated attention training framework comprising the context information and the local information. Updated model data 118 can be output by the integration component 106 or another system component. The updated model data 118 can be utilized to determine a result 120 derived from the image data 114. For example, the sequence of images (e.g., the image data 114) can be medical images associated with a defined patient and a determined result (e.g., the result 120) can be a diagnosis of a medical condition.

In certain embodiments, the initialization component 102, the localization component 104, and/or the integration component 106 can sequentially process the image data 114 based on classifications, correlations, inferences, and/or expressions associated with principles of artificial intelligence. For instance, the initialization component 102, the localization component 104, and/or the integration component 106, other classification models, as well as other system components, can employ an automatic classification system and/or an automatic classification process to determine which images can be the most helpful to determine a result and/or which portions of the images comprise the salient features on which focus should be directed. In one example, the initialization component 102, the localization component 104, and/or the integration component 106 can employ a probabilistic and/or statistical-based analysis (e.g., factoring into the analysis utilities and costs) to learn and/or generate inferences with respect to which images from the sequence of images to select and which portions of the selected images should be analyzed in detail. In an aspect, the system 100 can comprise an inference component (not shown) that can further enhance automated aspects of the model 116 and/or the updated model data 118 utilizing in part inference based schemes to facilitate learning and/or generating inferences associated with the selection of one or more images and/or portions of the images that should be focused on in order to increase a processing accuracy. The system 100 can employ any suitable machine-learning based techniques, statistical-based techniques, and/or probabilistic-based techniques. For example, the system 100 can employ expert systems, fuzzy logic, SVMs, Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, etc. In another aspect, the system 100 can perform a set of machine learning computations associated with training the model 116 and/or deriving the updated model data 118. For example, the system 100 can perform a set of clustering machine learning computations, a set of logistic regression machine learning computations, a set of decision tree machine learning computations, a set of random forest machine learning computations, a set of regression tree machine learning computations, a set of least square machine learning computations, a set of instance-based machine learning computations, a set of regression machine learning computations, a set of support vector regression machine learning computations, a set of k-means machine learning computations, a set of spectral clustering machine learning computations, a set of rule learning machine learning computations, a set of Bayesian machine learning computations, a set of deep Boltzmann machine computations, a set of deep belief network computations, and/or a set of different machine learning computations to perform sequential image processing for a sequence of images.

It is to be appreciated that the system 100 (e.g., the initialization component 102, the localization component 104, the integration component 106, as well as other system components) can perform processing of sequential images that cannot be performed by a human (e.g., is greater than the capability of a single human mind). For example, an amount of data processed, a speed of data processed, and/or data types of data processed by the system 100 (e.g., the initialization component 102, the localization component 104, the integration component 106, the model 116) over a certain period of time can be greater, faster, and different than an amount, speed, and data type that can be processed by a single human mind over the same period of time. The system 100 (e.g., the initialization component 102, the localization component 104, the integration component 106, the model 116) can also be fully operational towards performing one or more other functions (e.g., fully powered on, fully executed, performing various other computing functions, etc.) while also performing the above-referenced processing of sequential images. Moreover, the updated model data 118 generated and coordinated by the system 100 (e.g., the initialization component 102, the localization component 104, the integration component 106, the model 116) can include information that is impossible to obtain manually by a human. For example, a type of information included in the image data 114, a variety of information associated with the image data 114, and/or optimization of the image data 114 to generate and output the updated model data 118 and/or the result 120 based on sequential processing of the images can be more complex than information that can be obtained manually and processed by a human.

Figure 2:
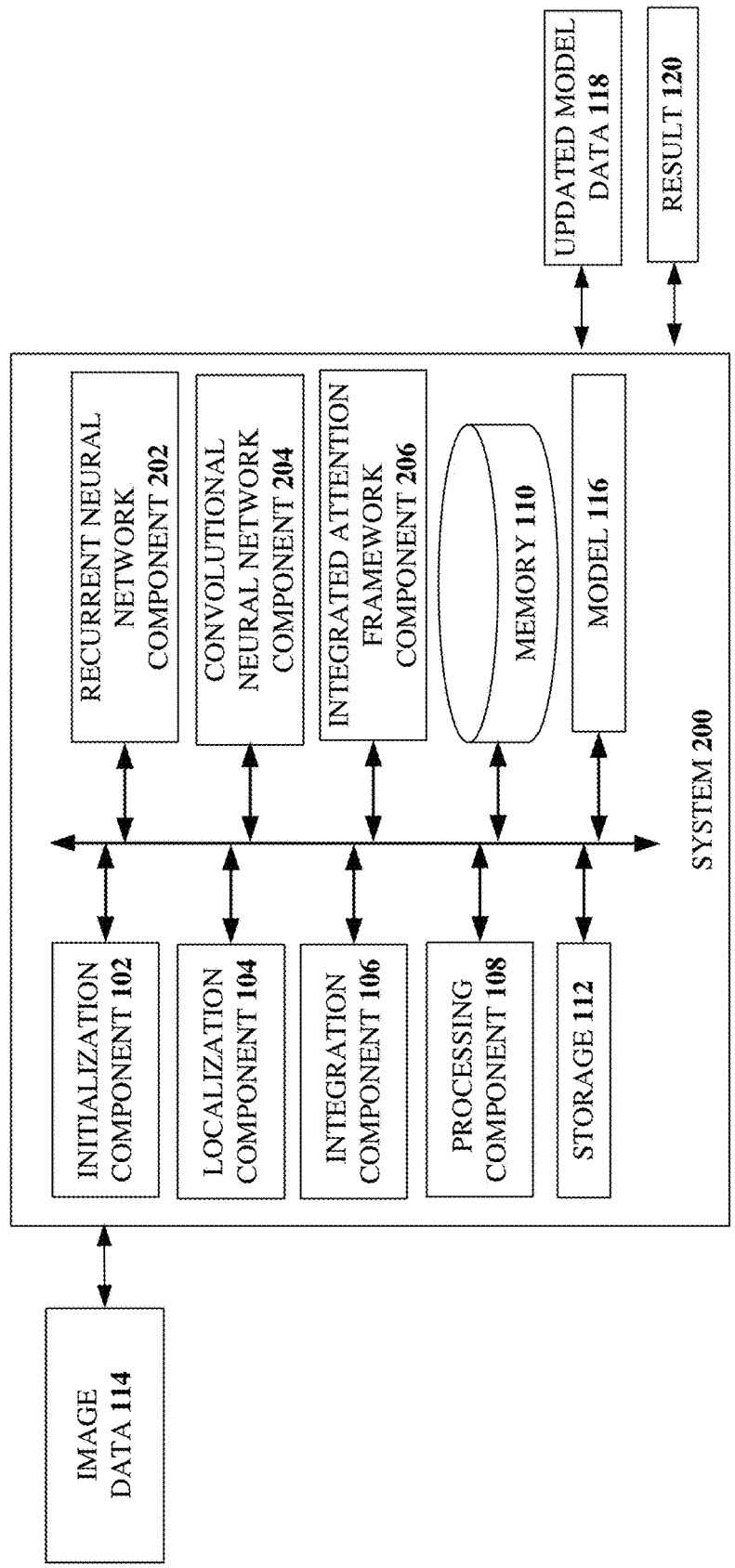
FIG. 2 illustrates a block diagram of an example, non-limiting system that facilitates attention based sequential image processing in accordance with one or more embodiments described herein.

FIG. 2 illustrates a block diagram of an example, non-limiting system 200 that facilitates attention based sequential image processing in accordance with one or more embodiments described herein. Repetitive description of like elements employed in other embodiments described herein is omitted for sake of brevity.

The system 200 can comprise one or more of the components and/or functionality of the system 100, and vice versa. The various aspects discussed herein can utilize neural networks to perform the sequential image processing. Neural networks, which can be machine learning models, can employ various layers of nonlinear units to predict an output or a result based on a received input (e.g., the image data 114, an output of the initialization component 102, another output of the localization component 104). For example, as discussed herein, neural networks can include one or more hidden layers. Respective outputs of the one or more hidden layers can be used as input to the next layer in the system 200. For example, image data 114 can be utilized as input to the initialization component 102 and an output of the initialization component 102 can be utilized as input to the localization component 104. Further, an output of the localization component 104 can be utilized as input to the integration component 106, which can output the result 120 of the sequential image processing.

The system 200 can comprise a recurrent neural network component 202, a convolutional neural network component 204, and an integrated attention framework component 206. According to some implementations, the recurrent neural network component 202 can be included, at least partially, in the initialization component 102 and can employ functionality of the initialization component 102, and vice versa. Further, the convolutional neural network component 204 can be included, at least partially, in the localization component 104 and can employ functionality of the localization component 104, and vice versa. In addition, the integrated attention framework component 206 can be included, at least partially, in the integration component 106 and can employ functionality of the integration component 106, and vice versa.

The recurrent neural network component 202 can perform training on the image data 114 (e.g., the sequence of images) prior to the self-attention based training applied by the initialization component 102. The recurrent neural network component 202 can apply principals of a recurrent neural network (RNN), which is a deep learning neural network. An example of an RNN is a Long Short-Term Memory (LSTM) model.

In further detail, an RNN is a class of artificial neural network that comprises units, and connections between units form a directed cycle. The directed cycle allows the RNN to exhibit dynamic temporal behavior. According to some implementations, RNNs can use an internal memory to process arbitrary sequences of inputs. With the ability to process arbitrary sequences of inputs, the RNNs can be applied to a variety of tasks including unsegmented, connected analysis of sequential images as discussed herein.

As an example, since the recurrent neural network component 202 applies principals of RNN, the recurrent neural network component 202, for sequential image processing, can be configured to learn (or can train the model 116 to learn) to identify images (e.g., a sequence of images) that contain a defined object, such as a lung (continuing the above example) by analyzing images that can be labeled as "healthy" or "unhealthy." Analytic results of the analysis can be used to identify a disease status in other images (e.g., the image data 114).

Further, according to various implementations, the recurrent neural network component 202 can employ principles of self-attention based RNN prediction. For example, self-attention based RNN prediction is an image classification method that can be based on a visual attention model. The self-attention theory is a self-regulation process that can occur as a result of becoming the subject to which the focus of attention is directed. Accordingly, the recurrent neural network component 202 can analyze the image data 114 based on a self-regulation process wherein the image data 114 become the attentional focus of the recurrent neural network component 202.

Figure 3:
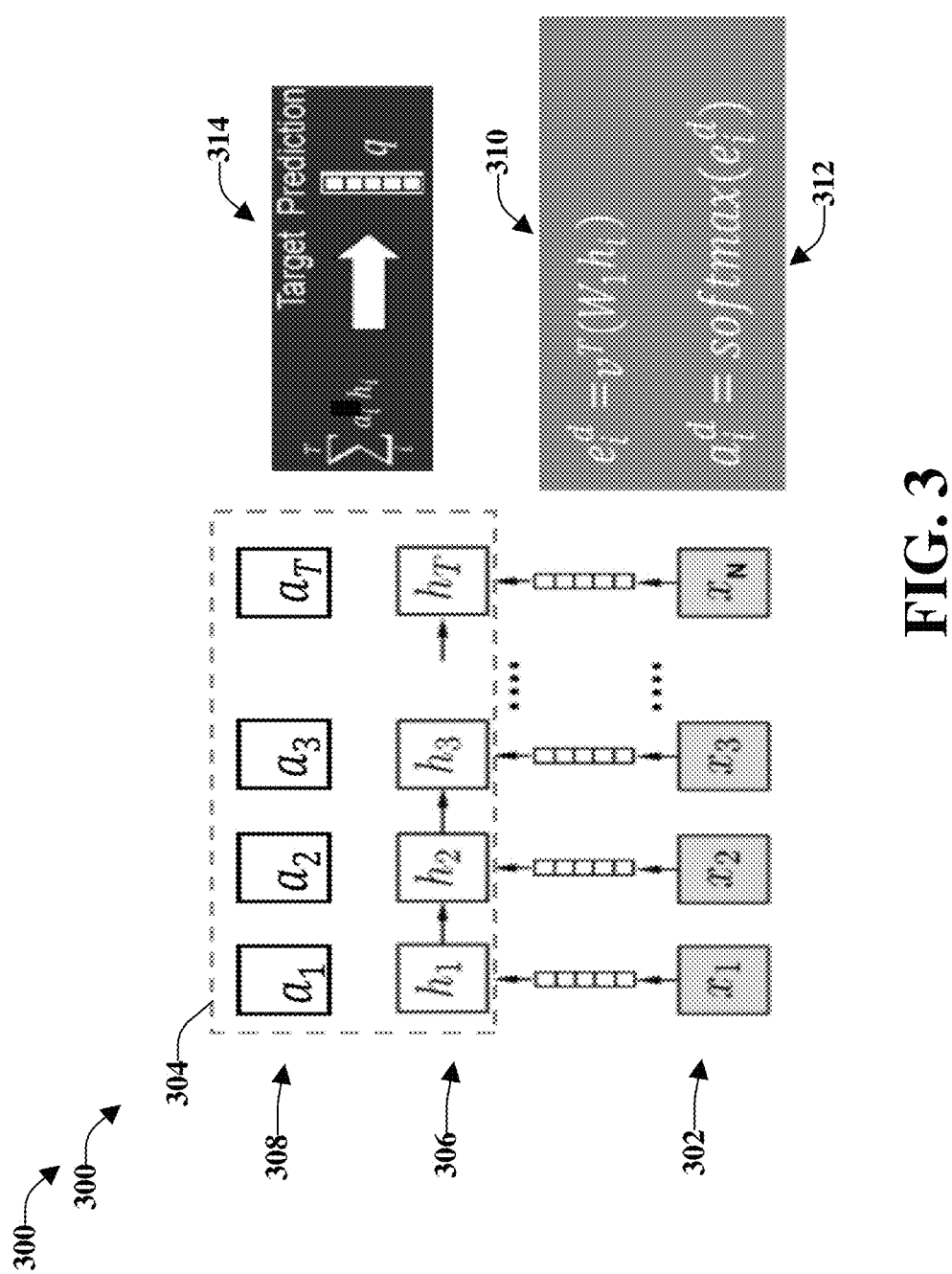
FIG. 3 illustrates a block diagram of an example, non-limiting system for self-attention based recurrent neural network prediction in accordance with one or more embodiments described herein.

To provide further detail, FIG. 3 illustrates a block diagram of an example, non-limiting system 300 for self-attention based recurrent neural network prediction in accordance with one or more embodiments described herein. Repetitive description of like elements employed in other embodiments described herein is omitted for sake of brevity.

The system 300 can comprise one or more of the components and/or functionality of the system 100 and/or the system 200, and vice versa. As illustrated one or more sequential image samples 302 (e.g., the image data 114) can be input to a model 304 (e.g., the model 116). The one or more sequential image samples 302 are illustrated as a first image $x_1$, a second image $x_2$, a third image $x_3$, through an Nth image $x_N$, where N is an integer equal to or greater then zero. For example, there can be three input images, less than three input images (although at least three input images are illustrated), or more than three input images.

Respective hidden layer states 306 can be determined for the one or more input images. For example, a first hidden layer state $h_1$ can be determined for the first image $x_1$, a second hidden layer state $h_2$ can be determined for the second image $x_2$, a third hidden layer state $h_3$ can be determined for the third image $x_3$, and a T hidden layer state $h_T$ can be determined for the Nth image $x_N$, where T is an integer equal to N.

Self-attention based training can be applied such that respective attention weights 308 can be applied to the one or more sequential image samples 302. The attention weights 308 can be utilized to determine which path is the most important for the local information and which time frame is important for one or more images of the sequential images. For example, as illustrated there can be a first attention $a_1$ for the first image $x_1$, a second attention $a_2$ for the second image $x_2$, a third attention $a_3$ for the third image $x_3$, and a T attention $a_T$ for the Nth image $x_N$. According to some implementations, a sum of the attention weights can be equal to one. Therefore, the one or more attention weights can indicate respective importance of the different time frames as given by a first equation 310:

$$e_i^d = v^T(W_1 h_i)$$ Equation 1.

where a is the attention, h is the input, $W_1$ is the weight, and v is the sigmoid or the activation section. According to some implementations, to determine the attention a, a softmax function (e.g., a normalized exponential function) can be utilized. For example, the following equation (e.g., a second equation 312) can be utilized:

$$a_i^d = \text{soft max}(e_i^d)$$ Equation 2.

To predict the pattern (e.g., a target prediction q), the following equation (e.g., a third equation 314) can be utilized:

$$\sum_i^T a_i h_i.$$ Equation 3

With continuing reference to FIG. 2, an output of the recurrent neural network component 202 can be utilized as an input to the convolutional neural network component 204 (e.g., an input to the localization component 104). For example, the output of the recurrent neural network component 202 can be a subset of images selected from the image data 114. For example, there can be hundreds of sequential images received as image data. Based on the self-attention RNN applied to the hundreds of sequential images, a subset of the images (e.g., twenty images) can be selected as the focus of attention (e.g., the relevant images), which can be output to the convolutional neural network component 204.

According to some implementations, the convolutional neural network component 204 can extract relevant features of the subset of images selected by the recurrent neural network component 202. For example, to extract the relevant features, the convolutional neural network component 204 can utilize small windows (e.g., bounding boxes) that travel over the image(s). Accordingly, the focus can be directed within the respective window, without distraction from other portions of the image. For example, the convolutional neural network component 204 can focus a high level of attention or a high resolution on the portion of the image within the window, while other portions of the image, not included in the window, can be given a low level of attention or a low resolution. The window can be readjusted over time such that all portions of the image can be analyzed by the convolutional neural network component 204.

Figure 4:
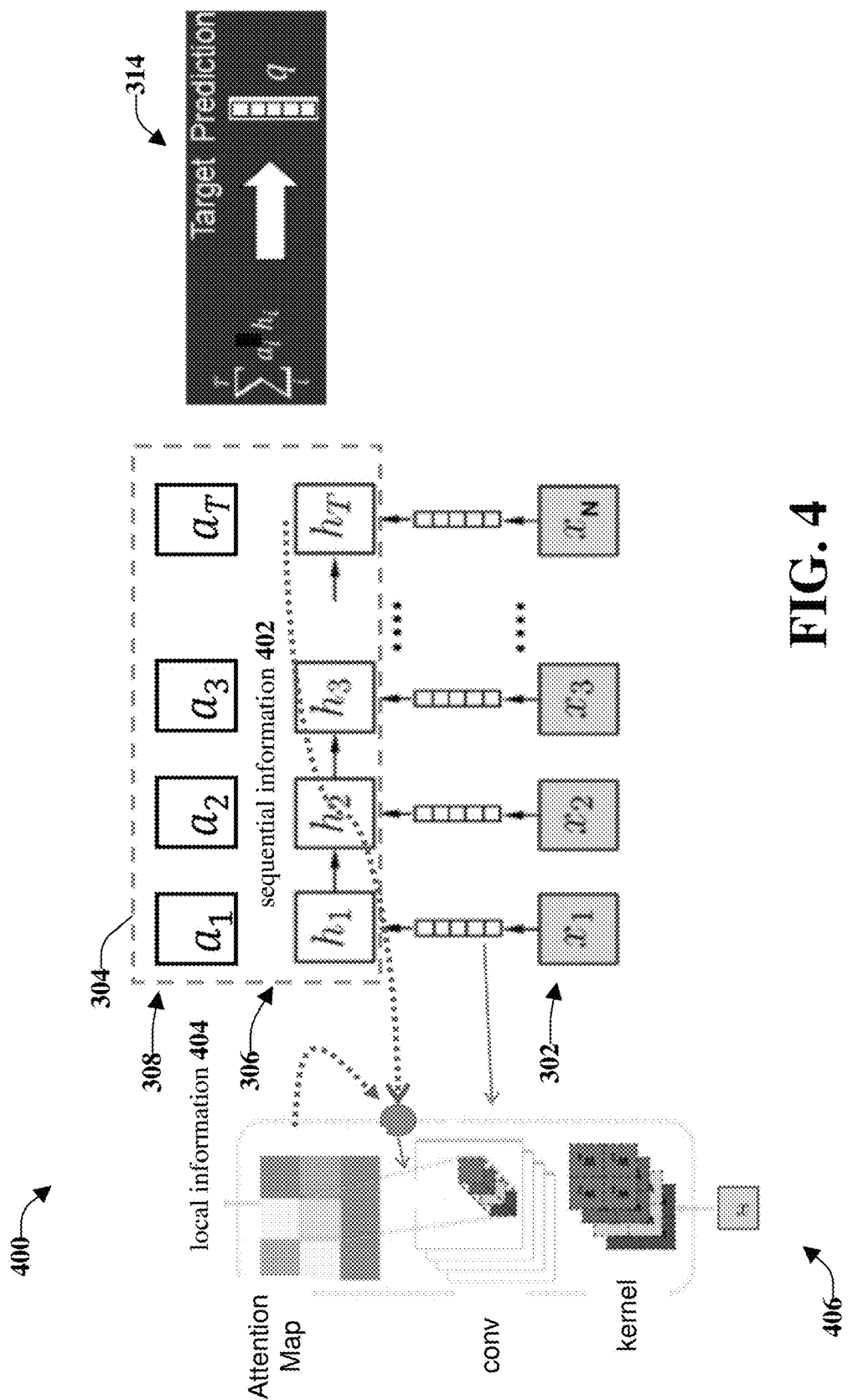
FIG. 4 illustrates a block diagram of an example, non-limiting system for attention convolutional neural network with sequential information in accordance with one or more embodiments described herein.

To provide additional detail, FIG. 4 illustrates a block diagram of an example, non-limiting system 400 for attention convolutional neural network with sequential information in accordance with one or more embodiments described herein. Repetitive description of like elements employed in other embodiments described herein is omitted for sake of brevity. The system 400 can comprise one or more of the components and/or functionality of the system 100, the system 200, and/or the system 300, and vice versa. As illustrated, sequential information 402 can be utilized as input. Further, attention to the location information 404 can be performed as discussed above. Illustrated to the left of the figure is a standard CNN framework 406.

An output of the convolutional neural network component 204 can be one or more specific portions or elements of the one or more images in the subset of images. For example, a first element in a first image of the subset of images can be identified by the convolutional neural network component 204. A second element and a third element in a second image of the subset of images can also be identified by the convolutional neural network component 204. Further, a fourth element in a third image of the subset of images can be identified by the convolutional neural network component 204. The one or more identified elements of the images of the subset of images can be the local information, which can be input to the integrated attention framework component 206.

The local information received from the convolutional neural network component 204 can be utilized by the integrated attention framework component 206 to determine the updated model data 118. For example, the integrated attention framework component 206 can train the model 116 on the local information to determine the updated model data 118. According to some implementations, the updated model data 118 can be utilized to determine the result 120 of the sequential image analysis.

Figure 5:
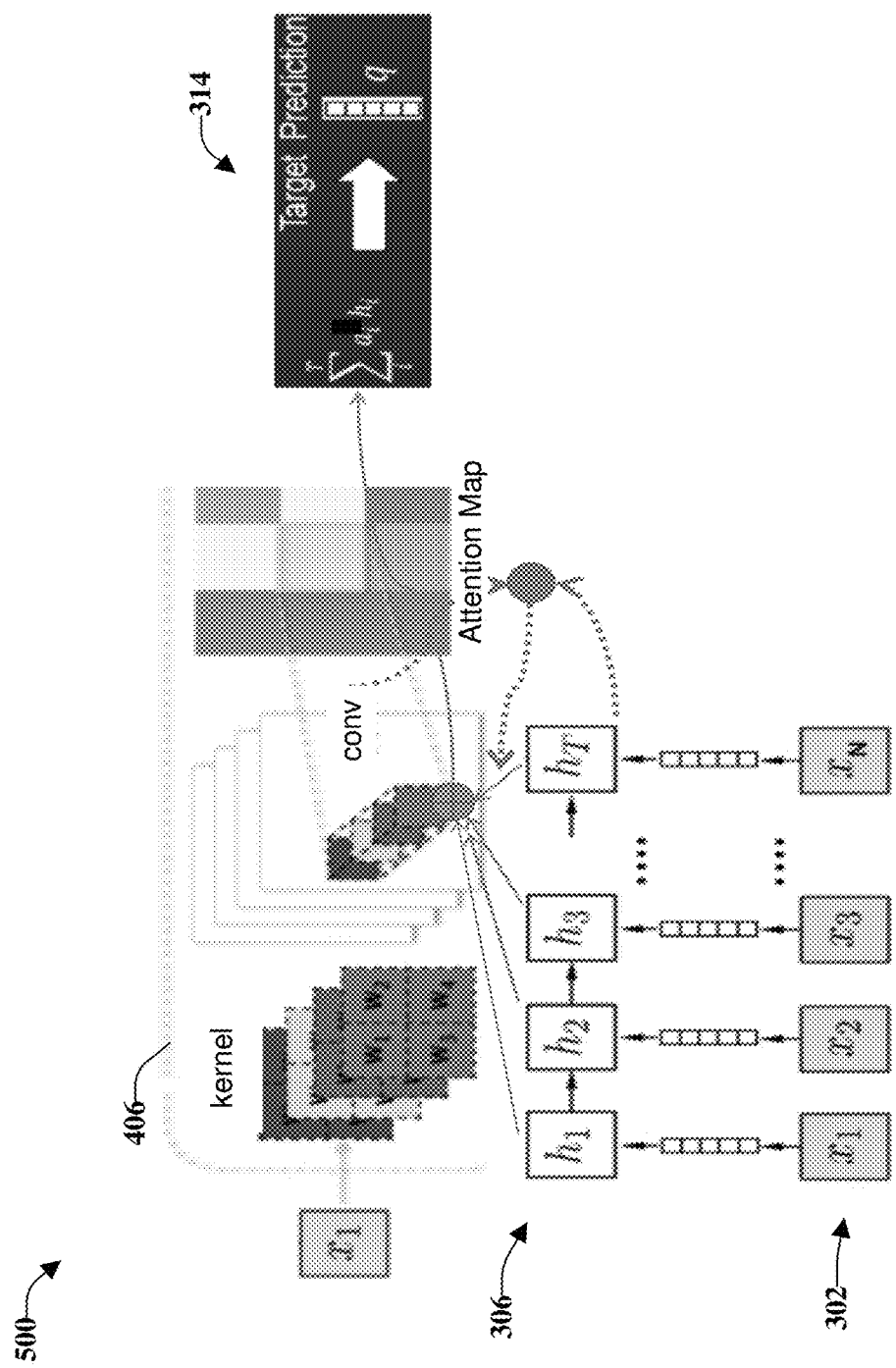
FIG. 5 illustrates a block diagram of an example, non-limiting system for end-to-end integrated attention framework training in accordance with one or more embodiments described herein.

To provide additional detail, FIG. 5 illustrates a block diagram of an example, non-limiting system 500 for end-to-end integrated attention framework training in accordance with one or more embodiments described herein. Repetitive description of like elements employed in other embodiments described herein is omitted for sake of brevity. The system 500 can comprise one or more of the components and/or functionality of the system 100, the system 200, the system 300, and/or the system 400, and vice versa. In FIG. 3, sequential information was used as input for the attention weight. Additional local information, such as feature map was also added, in FIG. 4, to update the sequential attention weight. As illustrated in FIG. 5, there is the local attention weight and the sequential attention weight, which represents the end-to-end between the integrated attention framework as discussed herein.

Figure 6:
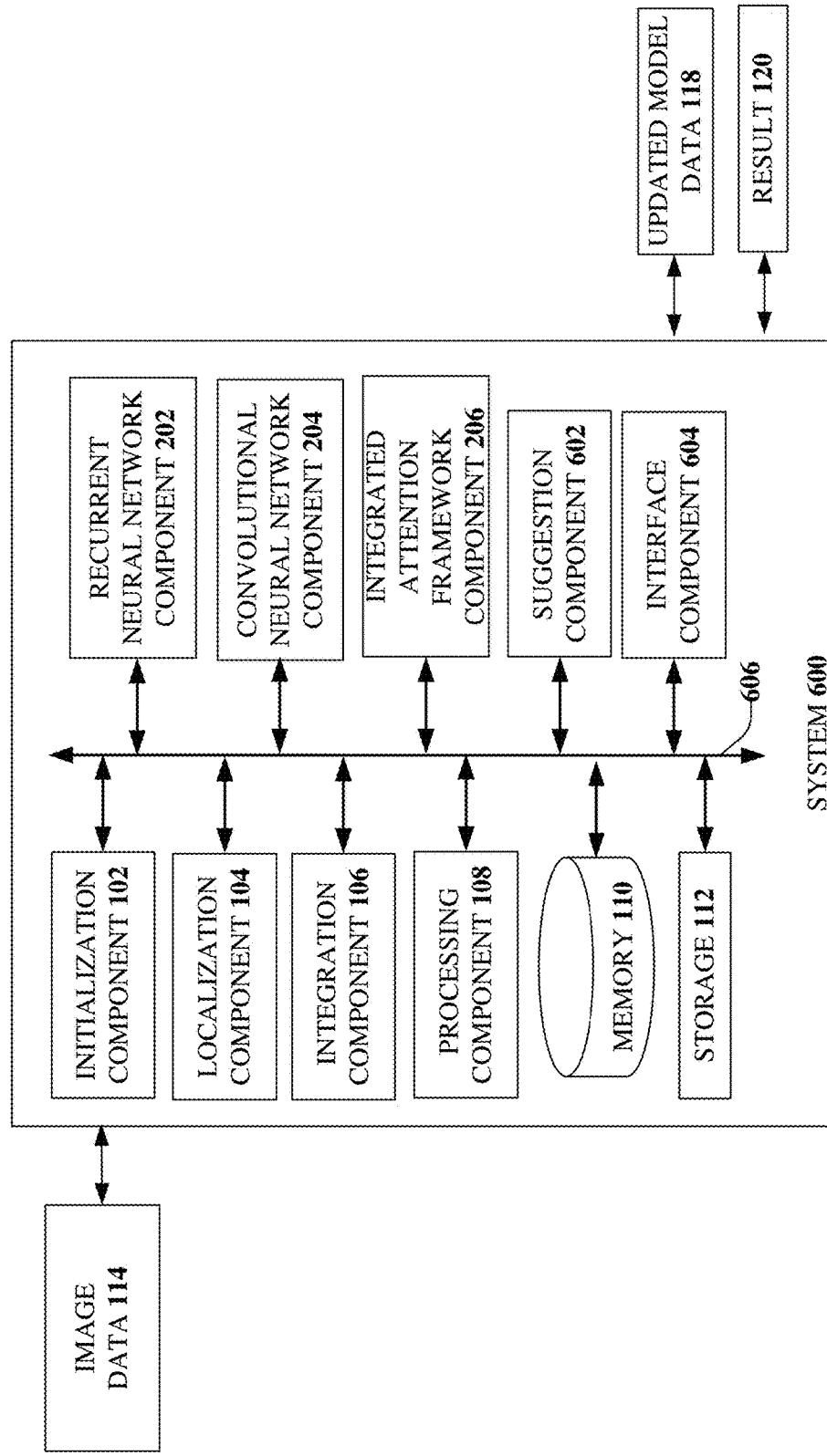
FIG. 6 illustrates a block diagram of an example, non-limiting system that determines a result based on a processing of a sequence of images in accordance with one or more embodiments described herein.

FIG. 6 illustrates a block diagram of an example, non-limiting system 600 that determines a result based on a processing of a sequence of images in accordance with one or more embodiments described herein. Repetitive description of like elements employed in other embodiments described herein is omitted for sake of brevity. The system 600 can comprise one or more of the components and/or functionality of the system 100, the system 200, the system 300, the system 400, and/or the system 500, and vice versa. The system 600 can comprise a suggestion component 602 and an interface component 604.

The initialization component 102 can perform self-attention based training on the model 116, which can comprise context information associated with a sequence of images (e.g., the image data 114). Images of the sequence of images can be selected during the self-attention based training performed by the initialization component 102. According to some implementations, the initialization component 102 can apply a recurrent neural network training on the sequence of images (e.g., via the recurrent neural network component 202) prior to the self-attention based training.

The localization component 104 can extract local information from the images selected during the self-attention based training based on the context information. For example, the localization component 104 can extract the local information based on an attention based prediction state sequence (e.g., via the convolutional neural network component 204). In another example, the localization component 104 can apply an attention convolutional neural network to extract the local information (e.g., via the convolutional neural network component 204). An application of the attention convolutional neural network can increase processing efficiency of the processor (e.g., the processing component 108).

According to some implementations, the localization component 104 can apply respective attention weights to the sequence of images to determine the local information. In an example, respective hidden layer state information for the sequence of images (e.g., image data 114) can be used as input to the localization component 104 to determine the respective attention weights. The local information can comprise features of the images determined by the localization component 104 to be relevant for training the model 116.

Further, the integration component 106 can update the model 116 based on an end-to-end integrated attention training framework comprising the context information and the local information. The suggestion component 602 can output the result 120 based on the model updated by the integration component 106. In an example, the sequence of images (e.g., the image data 114) can be medical images associated with a defined patient, and the result 120 output by the suggestion component 602 can be a diagnosis of a medical condition. According to some implementations, the result 120 output by the suggestion component 602 can include recommended treatment, recommended prescription medications, recommended physical therapy activities, or other recommended actions determined as a result of the medical diagnosis (e.g., the result 120).

The interface component 604 can be utilized to facilitate an output of the result 120 and to interact with entities external to the system. As utilized herein an entity can be one or more computers, the Internet, one or more systems, one or more commercial enterprises, one or more computers, one or more computer programs, one or more machines, machinery, one or more actors, one or more users, one or more customers, one or more humans, and so forth, hereinafter referred to as an entity or entities depending on the context.

According to some implementations, the interface component 604 (as well as other interface components discussed herein) can provide a graphical user interface (GUI), a command line interface, a speech interface, Natural Language text interface, and the like. For example, a Graphical User Interface (GUI) can be rendered that provides an entity with a region or means to load, import, select, read, and so forth, various requests and can include a region to present the results of the various requests. These regions can include known text and/or graphic regions that include dialogue boxes, static controls, drop-down-menus, list boxes, pop-up menus, as edit controls, combo boxes, radio buttons, check boxes, push buttons, graphic boxes, and so on. In addition, utilities to facilitate the information conveyance, such as vertical and/or horizontal scroll bars for navigation and toolbar buttons to determine whether a region will be viewable, can be employed. Thus, it might be inferred that the entity did want the action performed.

The entity can also interact with the regions to select and provide information through various devices such as a mouse, a roller ball, a keypad, a keyboard, a pen, gestures captured with a camera, a touch screen, and/or voice activation, for example. According to an aspect, a mechanism, such as a push button or the enter key on the keyboard, can be employed subsequent to entering the information in order to initiate information conveyance. However, it is to be appreciated that the disclosed aspects are not so limited. For example, merely highlighting a check box can initiate information conveyance. In another example, a command line interface can be employed. For example, the command line interface can prompt the entity for information by providing a text message, producing an audio tone, or the like. The entity can then provide suitable information, such as alphanumeric input corresponding to an option provided in the interface prompt or an answer to a question posed in the prompt. It is to be appreciated that the command line interface can be employed in connection with a GUI and/or Application Program Interface (API). In addition, the command line interface can be employed in connection with hardware (e.g., video cards) and/or displays (e.g., black and white, and Video Graphics Array (VGA)) with limited graphic support, and/or low bandwidth communication channels.

In some embodiments, the memory 110 can store the various data sources and/or structures of the system 600 (e.g., the model 116, the updated model data 118, the result 120, and the like). In other embodiments, the various data sources and structures of the system 600 can be stored in other memory (e.g., at a remote device or system), that can be accessible to the system 600 (e.g., via one or more networks). The system 600 can further include a device bus 606 that can communicatively couple the various components and data sources of the system 600 (e.g., the initialization component 102, the localization component 104, the integration component 106, the recurrent neural network component 202, the convolutional neural network component 204, the integrated attention framework component 206, the suggestion component 602, the interface component 604, the processing component 108, the memory 110, the storage 112). Examples of the processing component 108 and the memory 110, as well as other suitable computer or computing-based elements, can be found with reference to FIG. 10, and can be used in connection with implementing one or more of the systems or components shown and described in connection with FIG. 6 or other figures disclosed herein.

In some implementations, the system 600 and/or the various components and data sources of system 600 can be communicatively connected via one or more networks. Such networks can include wired and wireless networks, including but not limited to, a cellular network, a wide area network (WAD, e.g., the Internet) or a local area network (LAN). For example, the system 600 can communicate with an external device providing the image data 114 using virtually any desired wired or wireless technology, including but not limited to: wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Zigbee and other 802.XX wireless technologies and/or legacy telecommunication technologies, BLUETOOTH®, Session Initiation Protocol (SIP), ZIGBEE®, RF4CE protocol, WirelessHART protocol, 6LoWPAN (IPv6 over Low power Wireless Area Networks), Z-Wave, an ANT, an ultra-wideband (UWB) standard protocol, and/or other proprietary and non-proprietary communication protocols. The system 600 can thus include hardware (e.g., a central processing unit (CPU), a transceiver, a decoder), software (e.g., a set of threads, a set of processes, software in execution) or a combination of hardware and software that facilitates communicating information between the system 600 and external systems, sources and devices.

Figure 7:
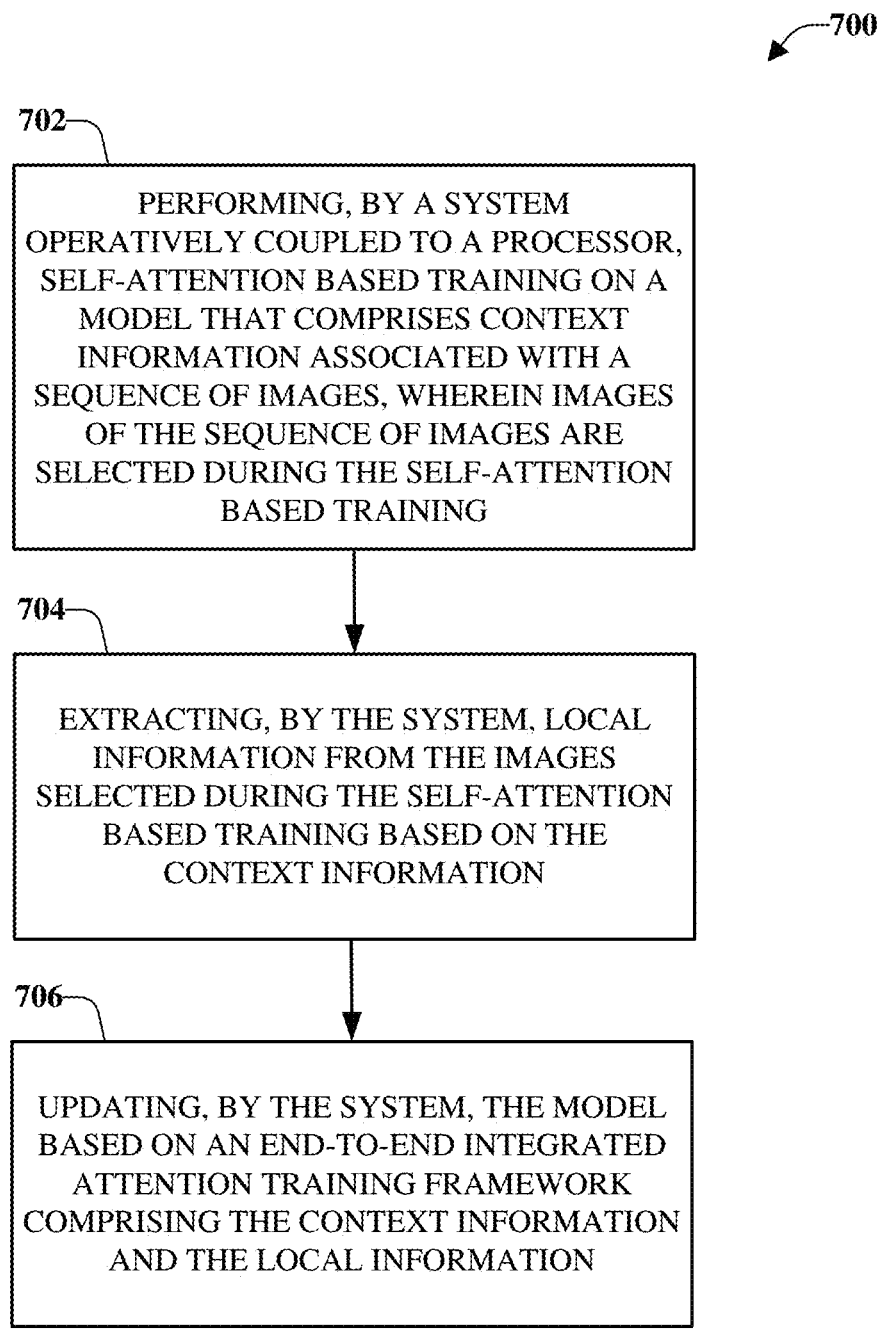
FIG. 7 illustrates a flow diagram of an example, non-limiting computer-implemented method that facilitates training a model in accordance with one or more embodiments described herein.

FIG. 7 illustrates a flow diagram of an example, non-limiting computer-implemented method 700 that facilitates training a model in accordance with one or more embodiments described herein. Repetitive description of like elements employed in other embodiments described herein is omitted for sake of brevity.

At 702 of the computer-implemented method 700, a system operatively coupled to a processor, can perform self-attention based training on a model that comprises context information associated with a sequence of images (e.g., via the initialization component 102). The images of the sequence of images can be selected during the self-attention based training.

Local information from the images selected during the self-attention based training can be extracted at 704 of the computer-implemented method 700 (e.g., via the localization component 104). The images can be extracted based on the context information. In an example, respective attention weights can be applied to the sequence of images.

According to some implementations, extracting the local information can comprise extracting the local information based on an attention based prediction state sequence. In accordance with some implementations, extracting the local information can comprise extracting features of the images determined to be relevant for updating the model. According to another implementation, extracting the local information can comprise applying, by the system, an attention convolutional neural network to the local information.

At 706 of the computer-implemented method, the model can be updated based on an end-to-end integrated attention training framework comprising the context information and the local information (e.g., via the integration component 106). A result associated with the sequence of images can be output upon or after the updating. The result can be based on the model. According to some implementations, the sequence of images can be medical images associated with a defined patient. Further to these implementations, the result can be a diagnosis of a medical condition.

Figure 8:
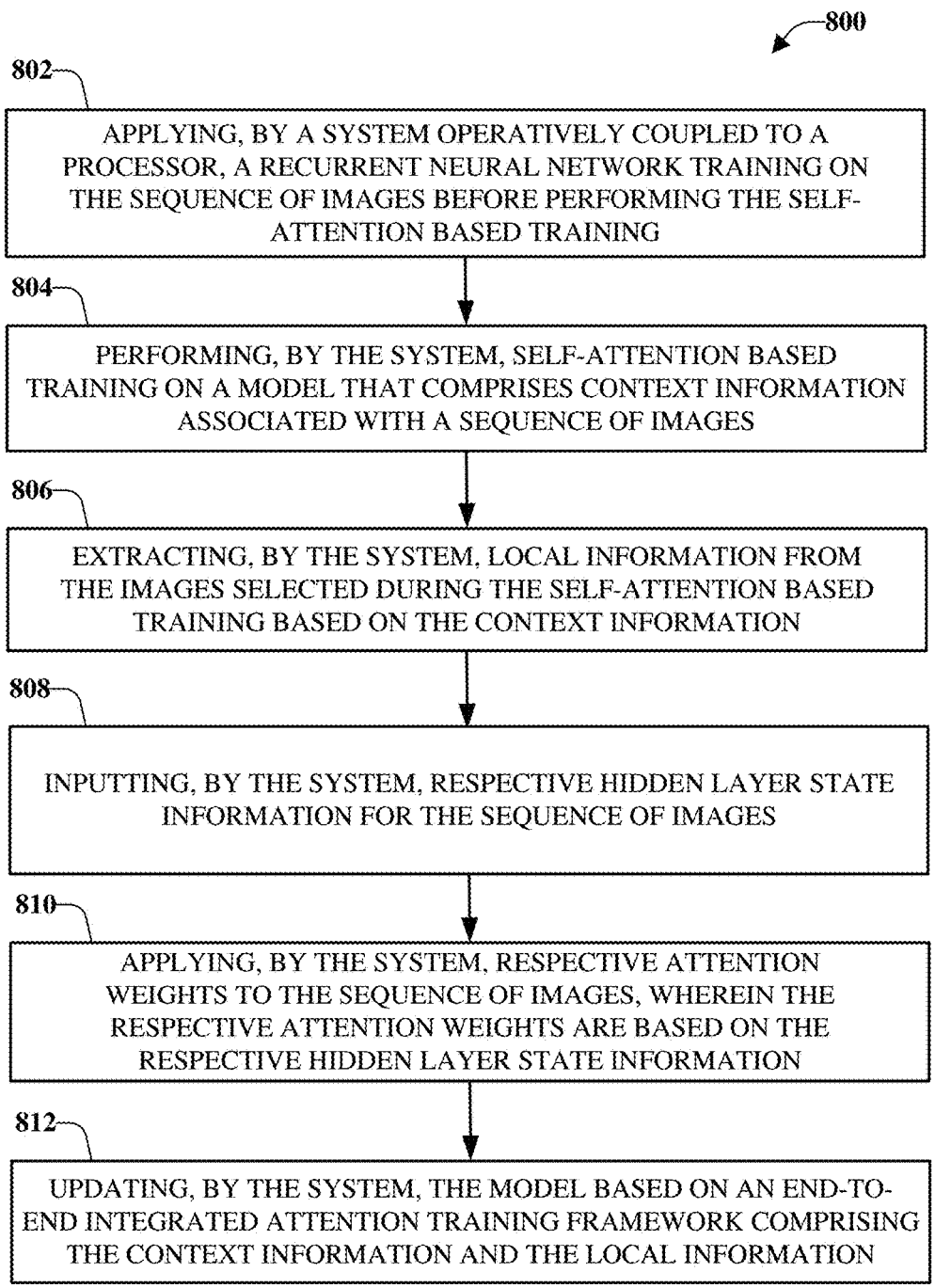
FIG. 8 illustrates a flow diagram of an example, non-limiting computer-implemented method that facilitates extracting local information to train a model in accordance with one or more embodiments described herein.

FIG. 8 illustrates a flow diagram of an example, non-limiting computer-implemented method 800 that facilitates extracting local information to train a model in accordance with one or more embodiments described herein. Repetitive description of like elements employed in other embodiments described herein is omitted for sake of brevity.

The computer-implemented method 800 can begin at 802 when a recurrent neural network training on a sequence of images can be applied by a system operatively coupled to a processor (e.g., via the initialization component 102). According to some implementations, the sequence of images can be medical images, however, the disclosed aspects are not limited to this implementation and other types of images can be utilized.

Self-attention based training can be performed, at 804 of the computer-implemented method 800, on a model that comprises context information associated with a sequence of images (e.g., via the recurrent neural network component 202). Images of the sequence of images can be selected during the self-attention based training.

At 806 of the computer-implemented method 800, local information can be extracted from the images selected during the self-attention based training based on the context information (e.g., via the localization component 104). To extract the location information, at 808 of the computer-implemented method 800, respective hidden layer state information for the sequence of images can be input into the model (e.g., via the localization component 104). Further, at 810 of the computer-implemented method 800, respective attention weights can be applied to the sequence of images (e.g., via the convolutional neural network component 204). The respective attention weights can be based on the respective hidden layer state information. Further, application of the respective attention weights can increase a processing efficiency of the processor.

The computer-implemented method 800 can continue at 812 with updating, by the system, the model based on an end-to-end integrated attention training framework comprising the context information and the local information (e.g., via the integrated attention framework component 206). According to an implementation, an output of the end-to-end integrated attention training framework can be a result of an analysis performed during the sequential image processing.

Figure 9:
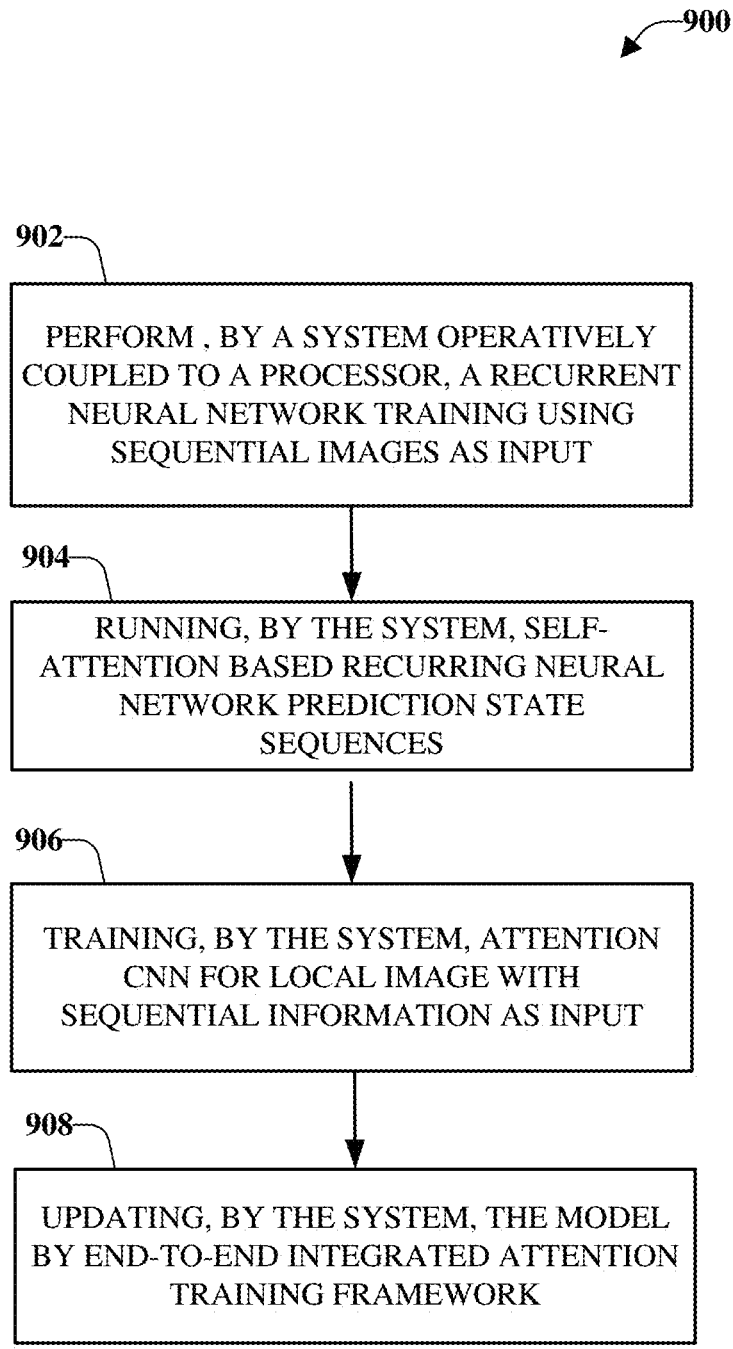
FIG. 9 illustrates a flow diagram of an example, non-limiting computer-implemented method that facilitates attention based sequential image processing in accordance with one or more embodiments described herein.

FIG. 9 illustrates a flow diagram of an example, non-limiting computer-implemented method 900 that facilitates attention based sequential image processing in accordance with one or more embodiments described herein. Repetitive description of like elements employed in other embodiments described herein is omitted for sake of brevity.

At 902 of the computer-implemented method 900, a system operatively coupled to a processor can perform RNN training using sequential images as input (e.g., via the recurrent neural network component 202). At 904 of the computer-implemented method 900, the system can run self-attention based RNN prediction state sequences (e.g., via the recurrent neural network component 202).

Further, at 906 of the computer-implemented method 900, attention convolutional neural network (CNN) for local image with sequential information as input can be trained by the system (e.g., via the convolutional neural network component 204). At 908 of the computer-implemented method, the system can update the model by end-to-end integrated attention training framework (e.g., via the integrated attention framework component 206). According to some implementations, the sequential attention can also use local information as input.

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Figure 10:
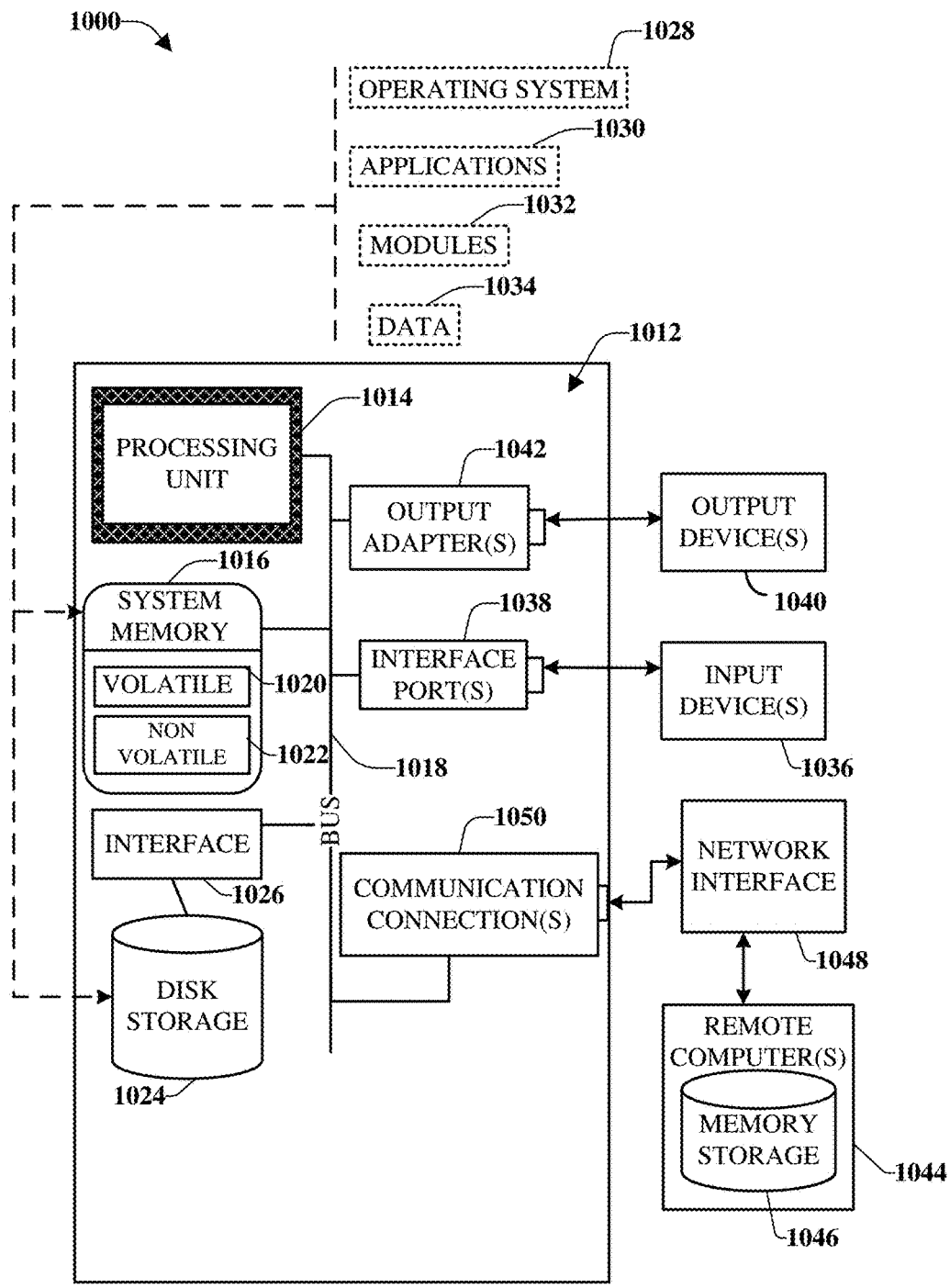
FIG. 10 illustrates a block diagram of an example, non-limiting operating environment in which one or more embodiments described herein can be facilitated.

In order to provide a context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. Repetitive description of like elements employed in other embodiments described herein is omitted for sake of brevity. With reference to FIG. 10, a suitable operating environment 1000 for implementing various aspects of this disclosure can also include a computer 1012. The computer 1012 can also include a processing unit 1014, a system memory 1016, and a system bus 1018. The system bus 1018 couples system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, is stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM)). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/nonvolatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface is typically used, such as interface 1026. FIG. 10 also depicts software that acts as an intermediary between users and the basic computer resources described in the suitable operating environment 1000. Such software can also include, for example, an operating system 1028. Operating system 1028, which can be stored on disk storage 1024, acts to control and allocate resources of the computer 1012. System applications 1030 take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port can be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a method of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create method for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other method to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has,"

"possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor that executes the computer executable components stored in the memory, wherein the computer executable components comprise:
an initialization component that performs self-attention based training on a model that comprises context information associated with a sequence of images, wherein images of the sequence of images are selected during the self-attention based training;
a localization component that extracts local information from the images selected during the self-attention based training based on the context information; and
an integration component that updates the model based on an end-to-end integrated attention training framework comprising the context information and the local information, wherein the localization component applies respective attention weights to the sequence of images, and wherein respective hidden layer state information for the sequence of images is used as input to the localization component to determine the respective attention weights.

2. The system of claim 1, wherein the localization component extracts the local information based on an attention based prediction state sequence.

3. The system of claim 1, wherein the local information comprises features of the images determined by the localization component to be relevant for training the model.

4. The system of claim 1 wherein the initialization component applies a recurrent neural network training on the sequence of images prior to the self-attention based training.

5. The system of claim 1, wherein the localization component applies an attention convolutional neural network to extract the local information, wherein application of the attention convolutional neural network increases a processing efficiency of the processor.

6. The system of claim 1, wherein the computer executable components further comprise a suggestion component that outputs a result based on the model updated by the integration component.

7. The system of claim 6, wherein the sequence of images are medical images associated with a defined patient, and wherein the result is a diagnosis of a medical condition.

8. A computer-implemented method, comprising:
performing, by a system operatively coupled to a processor, self-attention based training on a model that comprises context information associated with a sequence of images, wherein images of the sequence of images are selected during the self-attention based training;
extracting, by the system, local information from the images selected during the self-attention based training based on the context information; and
updating, by the system, the model based on an end-to-end integrated attention training framework comprising the context information and the local information, wherein the extracting the local information comprises:
inputting, by the system, respective hidden layer state information for the sequence of images; and
applying, by the system, respective attention weights to the sequence of images, wherein the respective attention weights are based on respective hidden layer state information and increases a processing efficiency.

9. The computer-implemented method of claim 8, wherein the extracting the local information comprises extracting the local information based on an attention based prediction state sequence.

10. The computer-implemented method of claim 8, wherein the extracting the local information comprises extracting features of the images determined to be relevant for updating the model.

11. The computer-implemented method of claim 8, further comprising:
applying, by the system, a recurrent neural network training on the sequence of images before performing the self-attention based training.

12. The computer-implemented method of claim 8, wherein the extracting the local information comprises applying, by the system, an attention convolutional neural network to the local information.

13. The computer-implemented method of claim 8, further comprising:
outputting, by the system, a result associated with the sequence of images, wherein the result is based on the model.

14. A computer program product that facilitates attention based sequential image processing, the computer program product comprising a computer readable storage medium having program instructions embodied therewith, the program instructions are executable by a processor to cause the processor to:
perform self-attention based training on a model that comprises context information associated with a sequence of images, wherein images of the sequence of images are selected during the self-attention based training;
extract local information from the images selected during the self-attention based training based on the context information;
update the model based on an end-to-end integrated attention training framework comprising the context information and the local information; and
determine respective attention weights for the sequence of images based on received hidden layer state information for the sequence of images, wherein the respective attention 15. The computer program product of claim 14, wherein the program instructions further cause the processor to:
extract the local information based on an attention based prediction state sequence.

16. The computer program product of claim 14, wherein the program instructions further cause the processor to:
apply an attention convolutional neural network to extract the local information.

* * * * *